United States Patent
Nishiura et al.

(10) Patent No.: US 8,980,444 B2
(45) Date of Patent: Mar. 17, 2015

(54) IRIDIUM COMPLEX AND ORGANIC LIGHT-EMITTING DEVICE INCLUDING THE SAME

(75) Inventors: Chiaki Nishiura, Kawasaki (JP); Masashi Hashimoto, Tokyo (JP); Shigemoto Abe, Yokohama (JP); Hiroya Nitta, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 458 days.

(21) Appl. No.: 13/514,025

(22) PCT Filed: Nov. 26, 2010

(86) PCT No.: PCT/JP2010/071752
§ 371 (c)(1),
(2), (4) Date: Jun. 5, 2012

(87) PCT Pub. No.: WO2011/070989
PCT Pub. Date: Jun. 16, 2011

(65) Prior Publication Data
US 2012/0235134 A1    Sep. 20, 2012

(30) Foreign Application Priority Data
Dec. 8, 2009    (JP) ................................ 2009-278967

(51) Int. Cl.
| | | |
|---|---|---|
| *H01L 51/54* | (2006.01) | |
| *C09K 11/06* | (2006.01) | |
| *C07F 15/00* | (2006.01) | |
| *H01L 51/00* | (2006.01) | |
| *H01L 51/50* | (2006.01) | |
| *H05B 33/14* | (2006.01) | |

(52) U.S. Cl.
CPC ............. *C07F 15/0033* (2013.01); *C09K 11/06* (2013.01); *H01L 51/0085* (2013.01); *H01L 51/5016* (2013.01); *H05B 33/14* (2013.01); *C09K 2211/1007* (2013.01); *C09K 2211/1044* (2013.01); *C09K 2211/185* (2013.01); *Y10S 428/917* (2013.01)
USPC .... 428/690; 428/917; 313/504; 257/E51.044; 548/103; 544/181

(58) Field of Classification Search
None
See application file for complete search history.

(56) References Cited

U.S. PATENT DOCUMENTS

2008/0038586 A1    2/2008    Nishizeki et al.

FOREIGN PATENT DOCUMENTS

| | | |
|---|---|---|
| CN | 100497358 C | 6/2009 |
| JP | 2005-53912 A | 3/2005 |
| JP | 2005-272411 A | 10/2005 |
| JP | 2007-208102 A | 8/2007 |
| JP | 2008-179617 A | 8/2008 |
| WO | 2005/123873 A | 12/2005 |

OTHER PUBLICATIONS

Govindaswamy, P. et al., "Self-assembled chloro-bridged metalloprismatic cations of the general formula", Inorganic Chemistry Communications, Oct. 1, 2007, pp. 1489-1492.

Zhang et al., "Synthesis and Phosphorescence of a New Greenish-blue Light-emitting Iridium (III) Bis (1-phenylpyridine) (1,2,4-triazole pyridine)", Chinese Journal of Luminescence, Feb. 28, 2007, vol. 28, No. 1, pp. 44-48.

Tae-Hyuk Kwon et al., "Color Tuning of Cyclometalated Iridium Complexes through Modification of Phenylpyrazole Derivatives and Ancillary Ligand Based on ab Initio Calculations", Organometallics, Feb. 25, 2005, vol. 24, No. 7, pp. 1578-1585.

*Primary Examiner* — Marie R. Yamnitzky
(74) *Attorney, Agent, or Firm* — Canon U.S.A., Inc. IP Division

(57) ABSTRACT

A novel iridium complex includes a ligand including a phenyl ring and a pyrazole ring. The phenyl group is bonded to a triazine ring to form a backbone of the novel iridium complex. An organic light-emitting device includes the novel iridium complex.

8 Claims, 3 Drawing Sheets

IRIDIUM COMPLEX AND ORGANIC LIGHT-EMITTING DEVICE INCLUDING THE SAME

TECHNICAL FIELD

The present invention relates to a novel iridium complex and an organic light-emitting device including the novel iridium complex.

BACKGROUND ART

Development in the area of organic light-emitting devices has been active. Development of organic light-emitting devices is linked with development of novel phosphorescent materials. PTL 1 discloses an iridium complex represented by the following structural formula:

[Chem. 1]

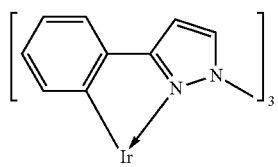

CITATION LIST

Patent Literature

PTL 1 Japanese Patent Laid-Open No. 2005-053912

SUMMARY OF INVENTION

Although PTL 1 discloses the structural formula, there is no specific descriptions about emission characteristics etc. Moreover, a compound represented by the structural formula above has a weak ligand field and such a compound is not expected to have good emission characteristics as a blue light-emitting material.

The present invention provides an iridium complex that emits blue phosphorescence and has good emission characteristics. An organic light-emitting device including such an iridium complex and having a high external quantum yield is also provided.

An aspect of the present invention provides an iridium complex represented by general formula (1):

[Chem. 1]

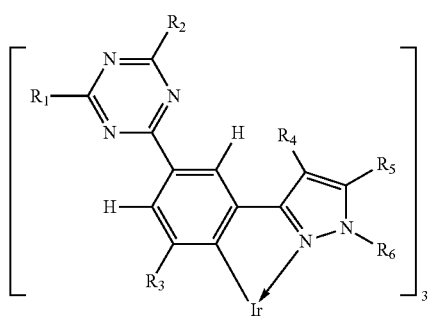

In formula (1), $R_1$ and $R_2$ each independently represent a group selected from a tert-butyl group, an adamantyl group, and a bicyclooctyl group; $R_3$ represents one selected from a hydrogen atom, a halogen atom, and a cyano group; $R_4$ and $R_5$ each independently represent one selected from a hydrogen atom, a halogen atom, a cyano group, an alkyl group, an alkoxy group, and an amino group; and $R_6$ represents an alkyl group.

DESCRIPTION OF EMBODIMENTS

Figure 1:
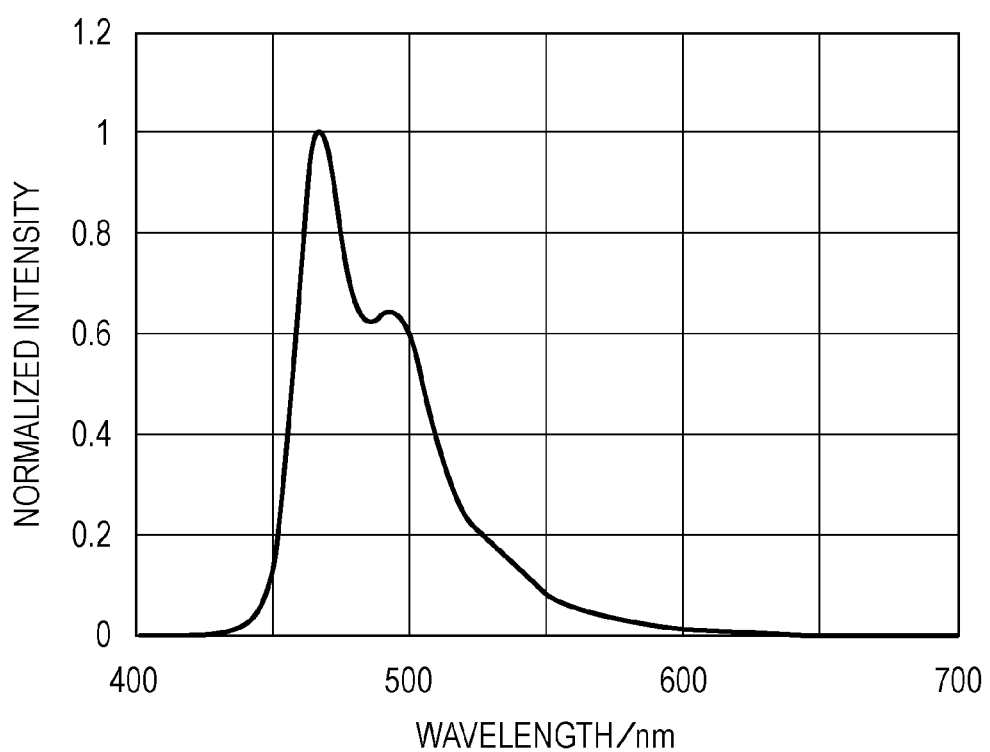
FIG. 1 is an emission spectrum diagram of Compound 1-1 according to an example of the present invention.

An iridium complex according to an embodiment of the present invention is represented by general formula (1) below.

[Chem. 3]

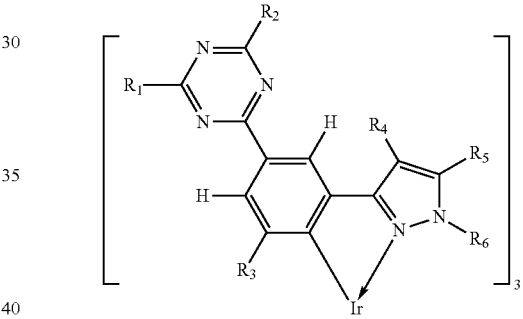

$R_1$ and $R_2$ each independently represent a group selected from a tert-butyl group, an adamantyl group, and a bicyclooctyl group. $R_3$ represents one selected from a hydrogen atom, a halogen atom, and a cyano group. $R_4$ and $R_5$ each independently represent one selected from a hydrogen atom, a halogen atom, a cyano group, an alkyl group, an alkoxy group, and an amino group. $R_6$ represents an alkyl group. Examples of the halogen atom represented by $R_3$ include a fluorine atom, a chlorine atom, a bromine atom, and an iodine atom. Substituents $R_4$ and $R_5$ may be the same as or different from each other. Examples of the halogen atom represented by $R_4$ and $R_5$ include a fluorine atom, a chlorine atom, a bromine atom, and an iodine atom. Examples of the alkyl group represented by $R_4$ and $R_5$ include a methyl group, an ethyl group, an isopropyl group, a tert-butyl group, and an adamantyl group.

Examples of the alkoxy group represented by $R_4$ and $R_5$ include a methoxyl group, an ethoxyl group, and a phenoxyl group. Examples of the amino group represented by $R_4$ and $R_5$ include a dimethylamino group and a diisopropylamino group. Examples of the alkyl group represented by $R_6$ include a methyl group, an ethyl group, an isopropyl group, a tert-butyl group, and an adamantyl group.

The iridium complex represented by general formula (1) has a ligand that has a skeleton in which a triazine ring, a phenyl ring, and a pyrazole ring excluding $R_1$ to $R_6$ and H are linked at particular sites. This skeleton is hereinafter referred to as "the ligand backbone in general formula (1)".

Because of the ligand backbone in general formula (1), the iridium complex emits blue phosphorescence.

There are four possible ligand structures A to D below constituted by a triazine ring, a phenyl ring, and a pyrazole ring. However, the structure C, i.e., the ligand backbone in general formula (1), is the favored backbone for blue light-emitting materials.

[Chem. 4]

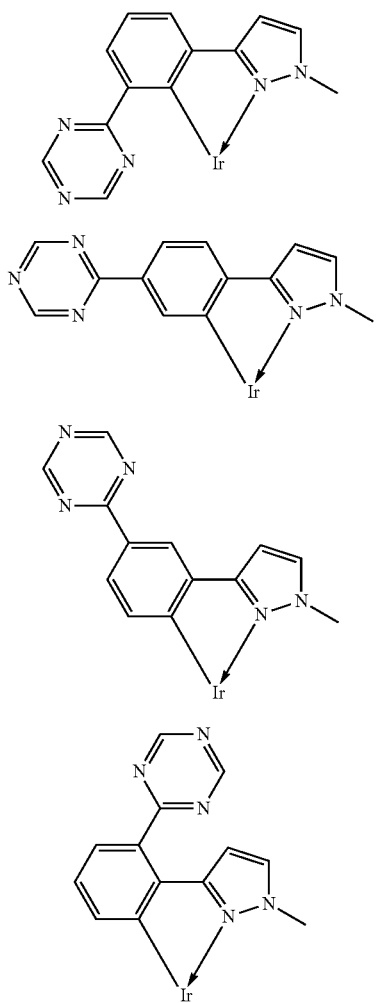

In order to obtain good emission characteristics in a blue region, a ligand that can form a stronger ligand field must be used.

In order to intensify the ligand field, it is important that the π back donation from the center metal, iridium, to the ligand be increased. π back donation is donation of electrons from the center metal of the complex to the ligand.

The inventors have realized that there are two crucial requirements for the π back donation derived from the electron-attracting triazine ring to work effectively. The structures A to D above all include iridium, a pyrazole ring, a phenyl ring, and a triazine ring.

Requirement 1: The substitution site of the triazine ring bonded to the phenyl group bonded to iridium is at the ortho or para position on the phenyl ring with respect to iridium.

Requirement 2: The triazine ring is coplanar with the phenyl ring.

In the structure B, iridium and the triazine ring are at meta positions on the phenyl ring and thus the structure B does not satisfy the requirement 1. In the structures A and D, the coplanarity between the phenyl ring and the triazine ring cannot be sterically maintained due to the steric repulsion between the iridium atom and the triazine ring at adjacent bonding sites in the structure A and the steric repulsion between the pyrazole ring and the triazine ring at adjacent bonding sites in the structure D. Thus, the structures A and D do not satisfy the requirement 2.

Only the structure C satisfies the two requirements and the ligand backbone in general formula (1) is favored for blue light-emitting materials.

Two hydrogen atoms of the phenyl ring, i.e., two H in general formula (1), are important for maintaining the coplanarity of the triazine ring and the phenyl ring.

The table below shows dihedral angles between the triazine ring and the phenyl ring determined by a molecular orbital method.

[Chem. 5]

| Structural formula | (phenyl) | (2,6-difluorophenyl) | (2,6-dimethylphenyl) |
|---|---|---|---|
| Dihedral angle between two rings | 0.00° | 42.9° | 49.7° |

The two ortho positions on the phenyl ring with respect to the triazine ring may be occupied by hydrogen atoms in order to maintain the coplanarity of the triazine ring and the phenyl ring.

Calculation of the dihedral angles was conducted using a commercially available electronic structure modeling program, Gaussian 03* Revision D.01. Structure optimization calculation of the ground state observed when a fluorine atom and a methyl group were introduced into the 2-position and the 6-position of the phenyl group was conducted using this program.

For the calculation, a density functional theory was employed as a quantum chemical calculation method, and B3LYP was used as the functional. For Gaussian 03, Revision D.01, 6-31G* was used as the basis function.

* Gaussian 03, Revision D.01,

M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

$R_1$ and $R_2$ in general formula (1) are each independently selected but may be the same substituent from the viewpoint of ease of synthesis.

Substituents $R_1$ and $R_2$ are provided to protect the triazine ring. Thus, it is important that the substituents $R_1$ and $R_2$ be bulky. In particular, $R_1$ and $R_2$ each independently represent a group selected from a tert-butyl group, an adamantyl group, and a bicyclooctyl group. For example, in order not to significantly increase the molecular weight of the iridium complex, $R_1$ and $R_2$ may each independently represent a tert-butyl group.

When an alkyl group having a large excluded volume is introduced, at least one of the following advantages can be expected:

1. High purity and high yield.
2. Suppression of coordinative ability of nitrogen atoms, suppression of capture of ionic impurities by lone pairs, and improved lifetime of organic light emitting device.
3. Suppression of intermolecular interaction and suppression of concentration quenching of the light-emitting material. Concentration quenching is a phenomenon in which the emission efficiency decreases at a high concentration.

$R_6$ in general formula (1) represents an alkyl group. This means that $R_6$ is not a hydrogen atom. When $R_6$ is a hydrogen atom, by-products derived from hydrogen tautomers occur during the synthesis of the complex. From a viewpoint of synthetic yield of the complex, a substituent having a small excluded volume is preferred. For example, a methyl group is preferred.

The iridium complex of this embodiment can be used as a blue phosphorescence emitting-material. Thus, the iridium complex is suitable as a light-emitting material of an organic light-emitting device. The organic light-emitting device is described below. The iridium complex of this embodiment has a band gap sufficient for use as a host material of an emission layer of an organic light-emitting device that emits green or red light.

Specific examples of the iridium complex are as follows.

[Chem. 6]

Example compound 1-1

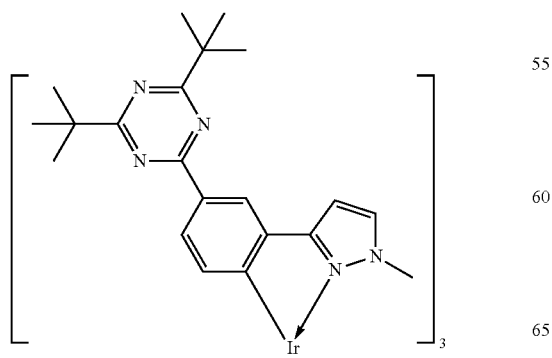

-continued

Example compound 1-2

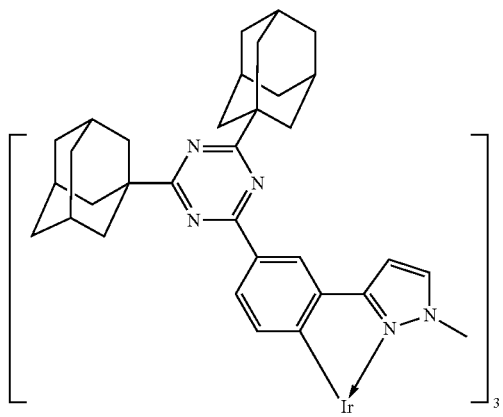

Example compound 1-3

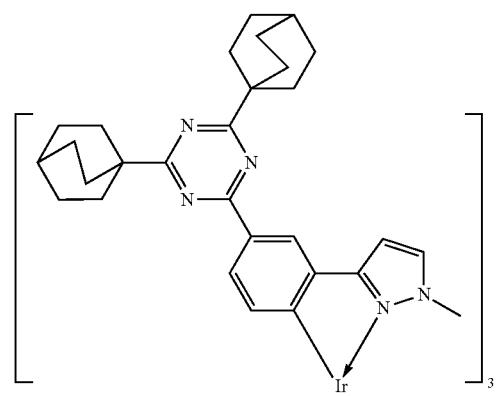

[Chem. 7]

Example compound 2-1

Example compound 2-2
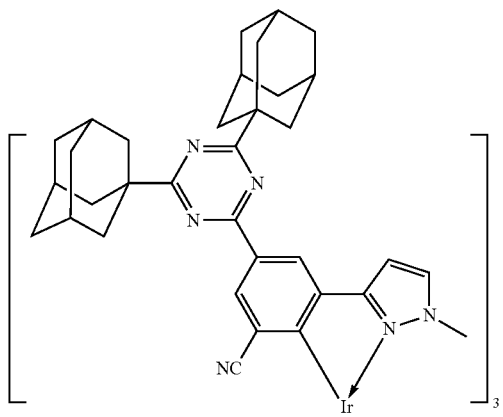
Example compound 2-3
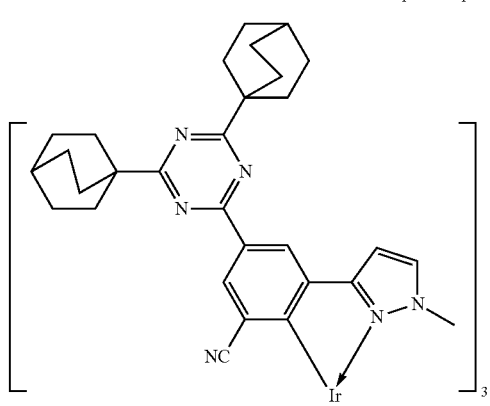
Example compound 2-4
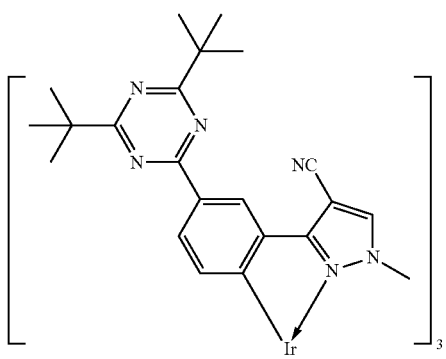
Example compound 2-5
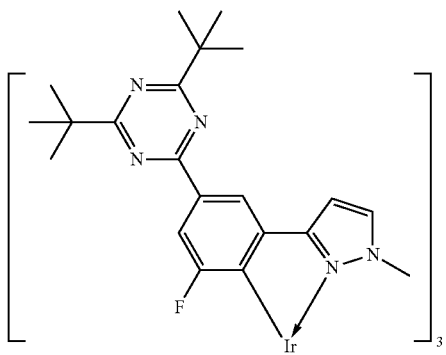
Example compound 2-6
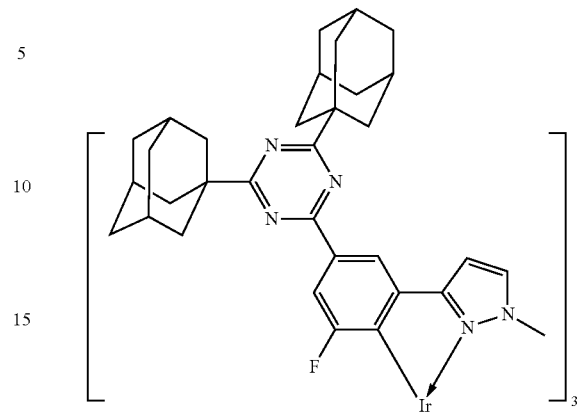
Example compound 2-7
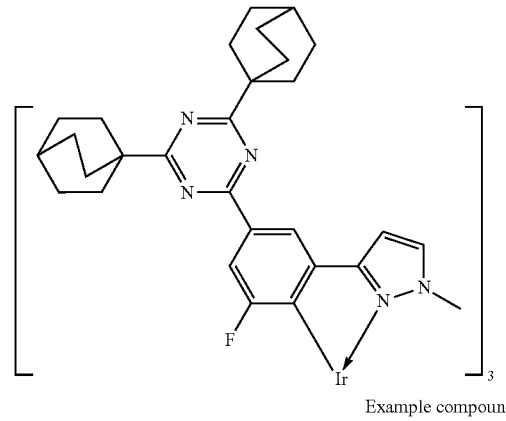
Example compound 2-8
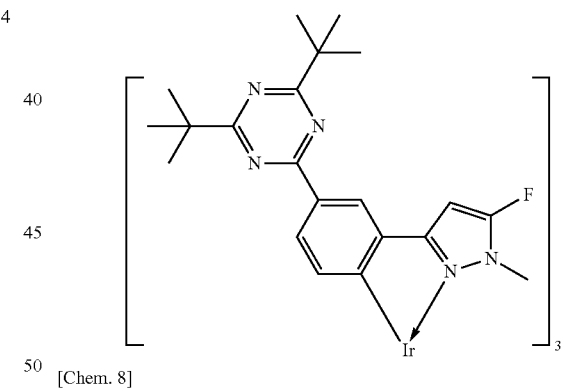
[Chem. 8]
Example compound 3-1
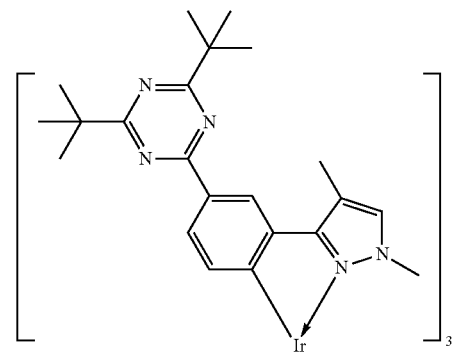

Example compound 3-2
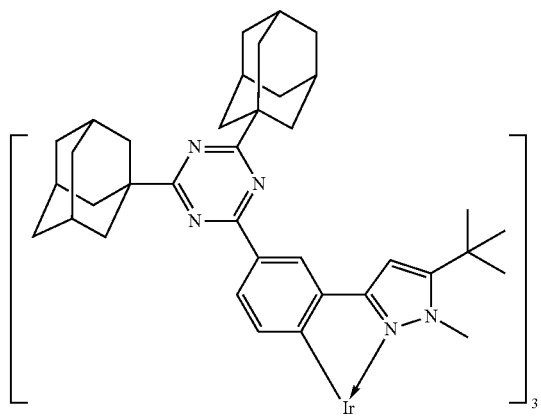
Example compound 3-3
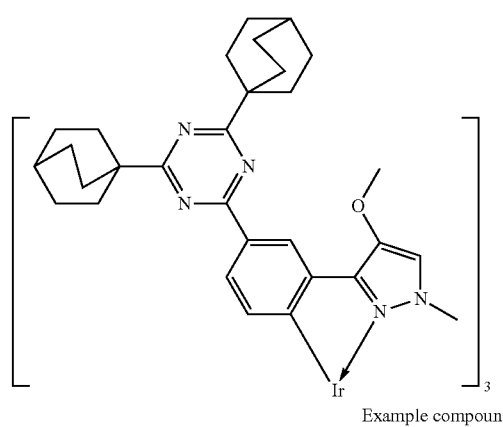
Example compound 3-4
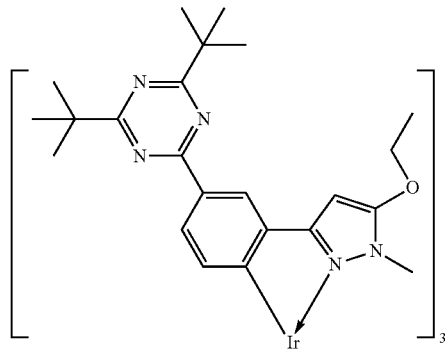
Example compound 3-5
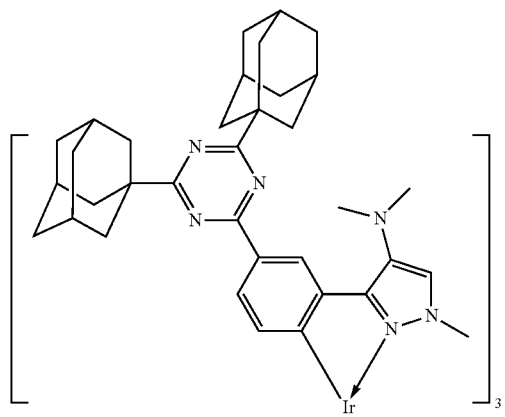
Example compound 3-6
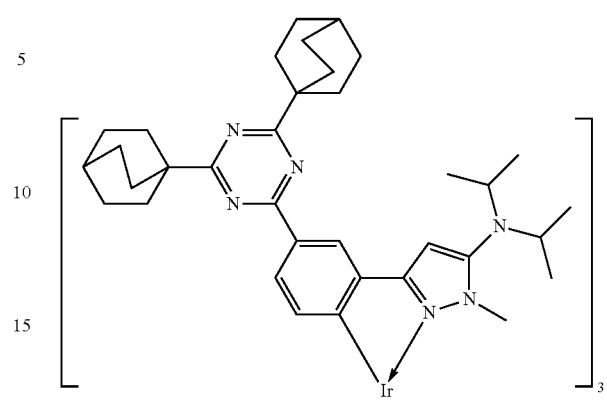
[Chem. 9]
Example compound 4-1
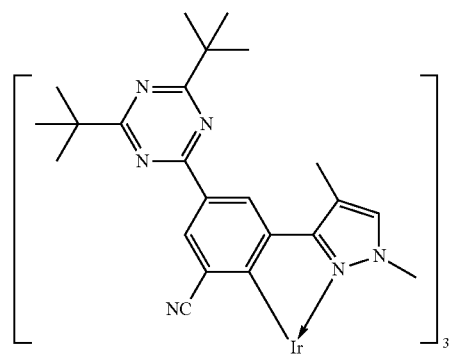
Example compound 4-2
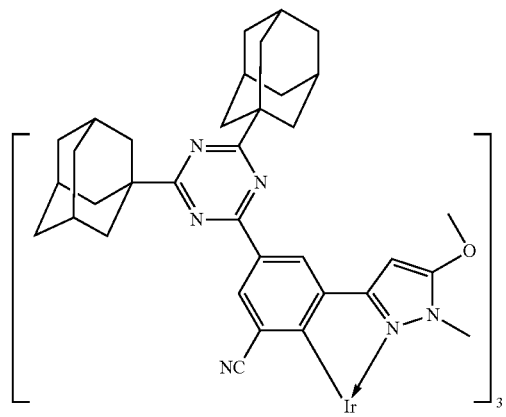

Example compound 4-3

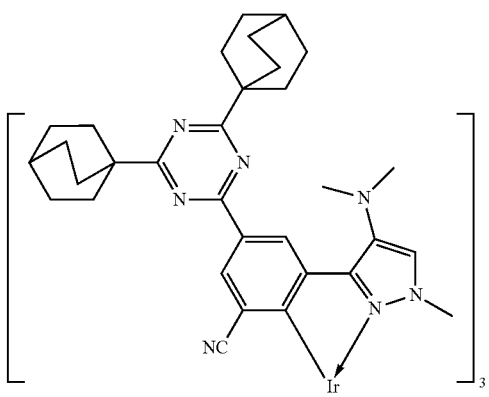

Example compound 4-4

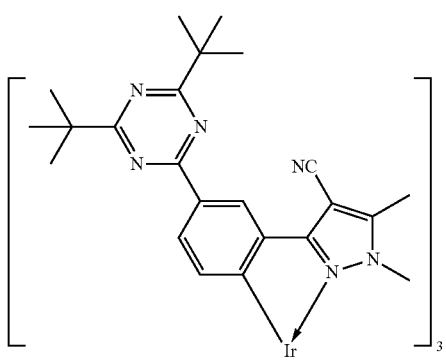

Example compound 4-5

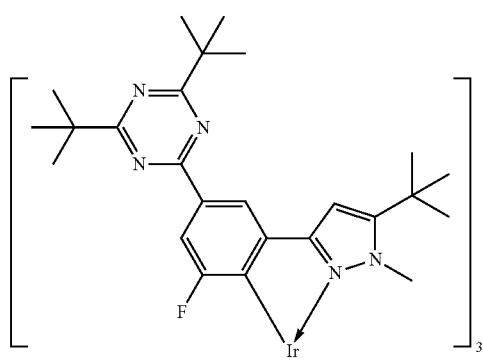

Example compound 4-6

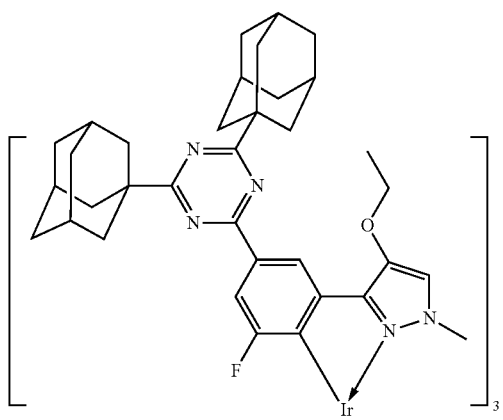

Example compound 4-7

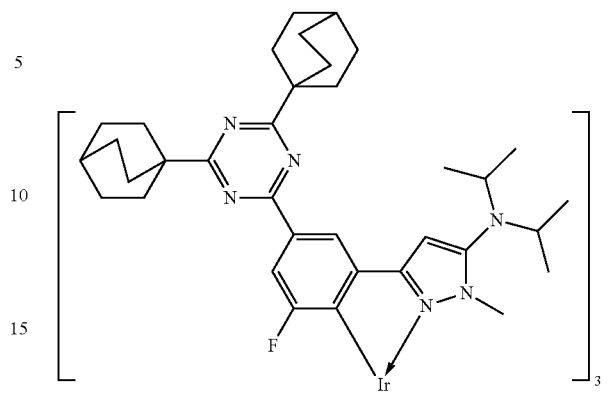

Example compound 4-8

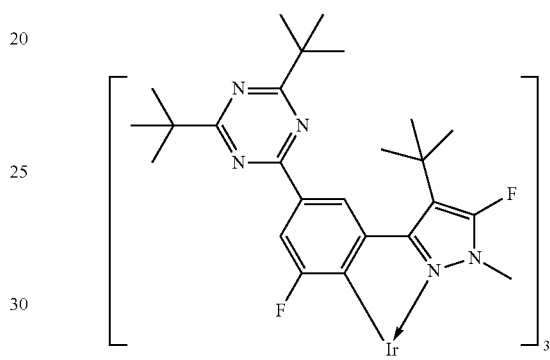

The iridium complex of this embodiment can be used as a material for an organic light-emitting device. The iridium complex may be used as a guest or host material of an emission layer of an organic light-emitting device. The organic light-emitting device includes a pair of electrodes opposing each other and an emission layer interposed between the electrodes. The organic light-emitting device may further include a layer or layers other than the emission layer. The iridium complex of this embodiment can be used in the emission layer and any of layers other than the emission layer, i.e., an electron transport layer, an electron injection layer, a hole transport layer, a hole injection layer, and a hole/exciton blocking layer.

A host material is a material that has the largest weight ratio among compounds constituting the emission layer and a guest material is a material that has a weight ratio smaller than that of the host material among the compounds constituting the emission layer.

The iridium complex of this embodiment may be used as a guest material of an emission layer of an organic light-emitting device. In particular, the iridium complex is preferably used as a guest material of a blue light-emitting device.

The emission wavelength can be changed by introducing a substituent into the backbone of the iridium complex of this embodiment.

When the iridium complex of this embodiment is used as a guest material of the emission layer, a host material having a higher LUMO level than the iridium complex, i.e., a host material having a LUMO level closer to the vacuum level, may be used. This is because when the iridium complex has a low LUMO level, the host material in the emission layer supplied with electrons can more smoothly give the electrons to the guest material, i.e., the iridium complex. LUMO level is an abbreviation of a lowest unoccupied molecular orbital level. HOMO level is an abbreviation of a highest occupied molecular orbital level. Further descriptions of the host material and the guest material are provided below.

Next, synthetic examples of the iridium complex of this embodiment are described by using synthetic examples of the ligand.

Synthetic Route

First, an example of synthesizing a ligand is described.

Synthetic Example of Ligand

Scheme 1

[Chem. 10]

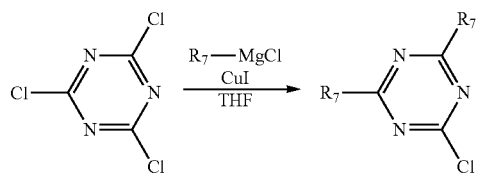

Various substituents can be introduced by changing the Grinard reagent, $R_7$—MgCl.

Scheme 2

[Chem. 11]

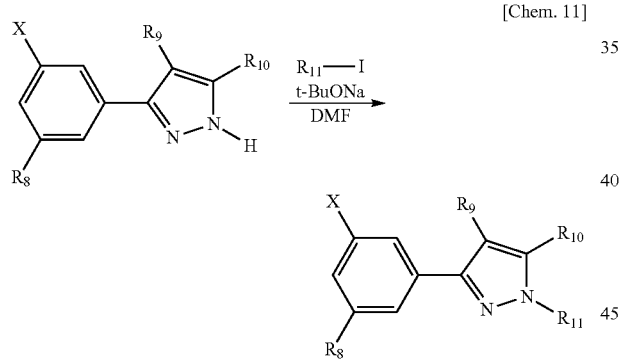

Various ligands can be synthesized by using a halogenated raw material with substituents introduced into $R_8$ to $R_{10}$. Various substituents can be introduced by changing the halide, $R_{11}$—I.

Scheme 3

[Chem. 12]

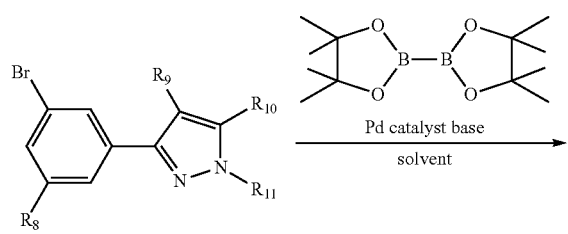

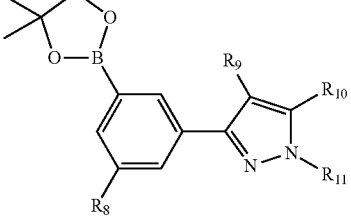

The halide used as a raw material is not limited to one into which bromine is introduced and may be, for example, one into which iodine or triflate is introduced. The product may be boronic acid, for example.

Scheme 4

[Chem. 13]

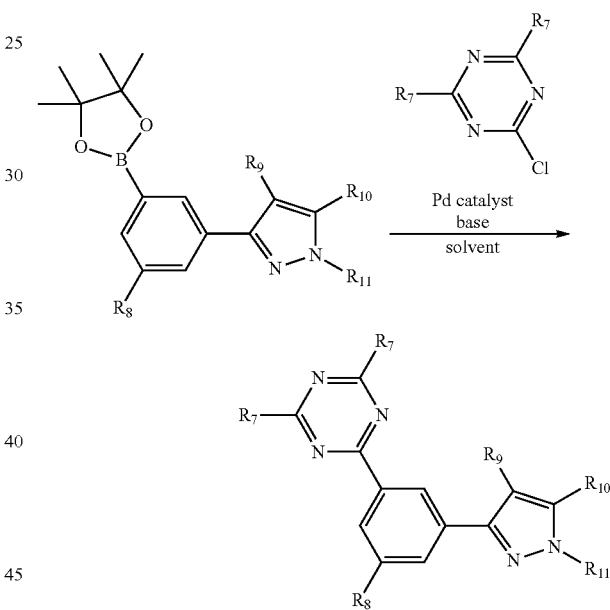

Various ligands can be synthesized by choosing the halogenated triazine synthesized in Scheme 1 and the boronic acid derivative having a 3-phenylpyrazole backbone synthesized in Scheme 3.

Next, synthetic examples of the iridium complex are described.

Synthetic Examples of Iridium Complex

Two examples of synthesizing iridium complexes are described below.

Example of 1-Step Synthesis

An example of 1-step synthesis using an iridium tris(acetylacetonate) complex as a raw material is described.

Scheme 5

[Chem. 14]

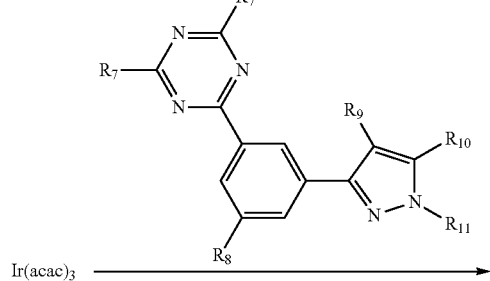

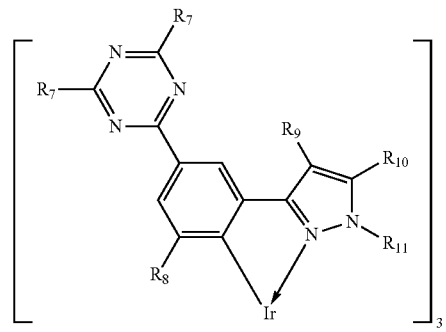

Although the solvent is not particularly specified, a protic solvent having a high boiling point, such as ethylene glycol and glycerol, is preferred.

Example of 3-Step Synthesis

An example of 3-step synthesis using iridium trichloride as a raw material is described below.

Scheme 6

[Chem. 15]

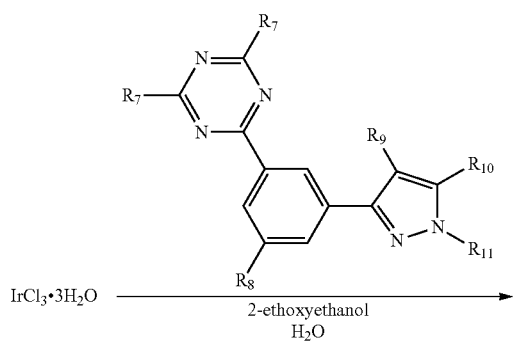

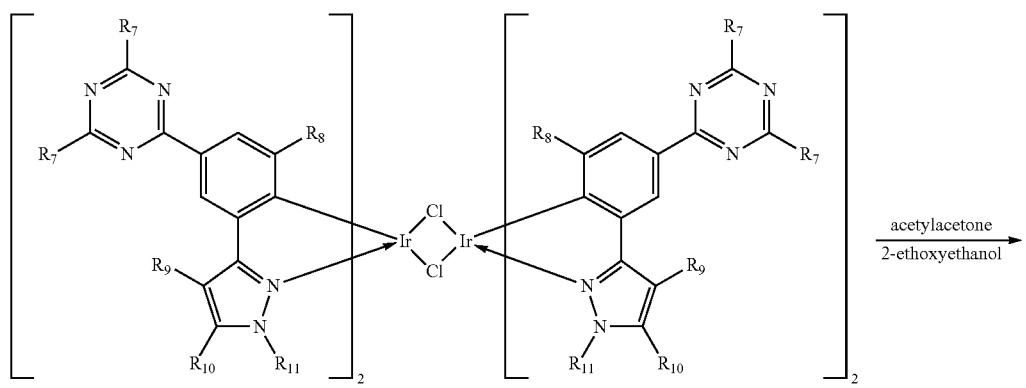

-continued

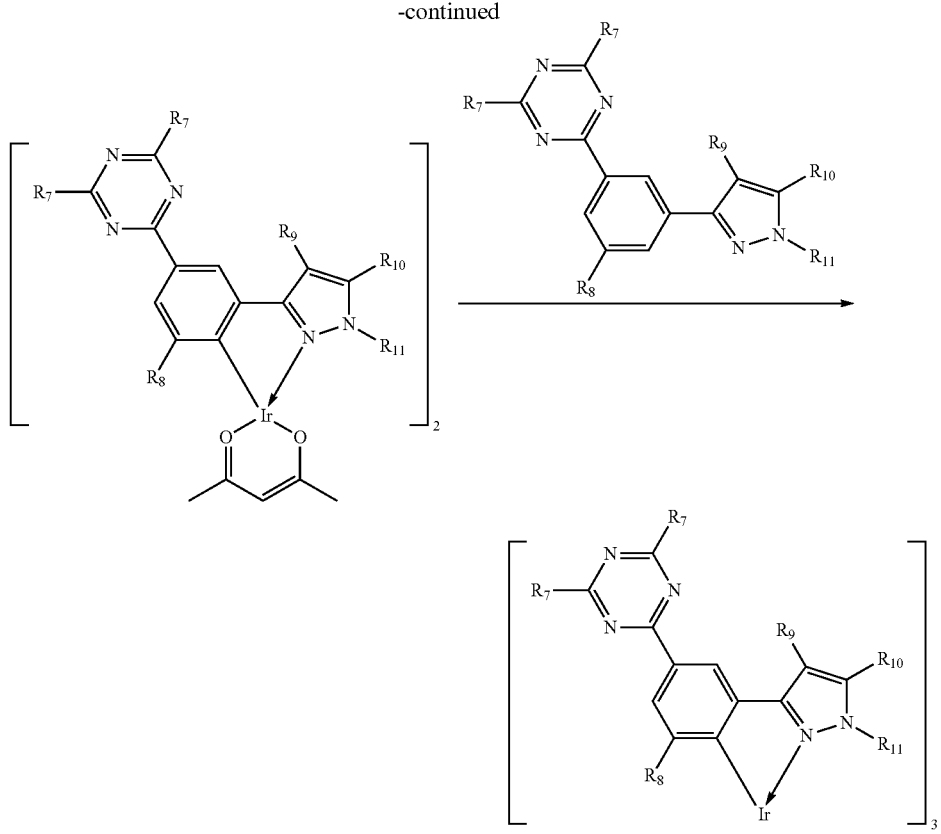

In the reaction of the third step in this scheme, ethylene glycol or glycerol may be used or no solvent may be used.

Next, an organic light-emitting device according to an embodiment of the present invention is described.

An organic light-emitting device according to one embodiment of the present invention includes a pair of electrodes and an organic compound layer interposed between the pair of electrodes. The pair of electrodes may be an anode and a cathode. A forward electric field necessary for causing emission and a reverse electric field may be applied to the pair of electrodes.

The organic compound layer contains the iridium complex of an embodiment.

The organic light-emitting device may further include an organic compound layer or layers in addition to this organic compound layer.

The organic light-emitting element includes an emission layer between the anode and the cathode. The emission layer may be the organic compound layer containing the iridium complex or may be constituted by the organic compound layer containing the iridium complex and a different organic compound layer. The organic compound layer containing the iridium complex may be an emission layer or a layer other than the emission layer. For example, at least one of a hole injection layer, a hole transport layer, a hole/exciton blocking layer, an electron transport layer, and an electron injection layer may contain the iridium complex.

The combination of the organic compound layer containing the iridium complex and other organic compound layers may be adequately selected. The number of other organic compound layers may be two or more.

The arrangement of the anode, the cathode, and the layers that lie between the anode and the cathode of the organic light-emitting device of this embodiment will now be described.

A first layer arrangement includes an anode, an emission layer, and a cathode stacked in that order. A second layer arrangement includes an anode, a hole transport layer, an electron transport layer, and a cathode stacked in that order. If emission is observed between the hole transport layer and the electron transport layer, the hole transport layer and the electron transport layer can be considered to constitute the emission layer. A third layer arrangement includes an anode, a hole transport layer, an emission layer, an electron transport layer, and a cathode stacked in that order. A fourth layer arrangement include an anode, a hole injection layer, a hole transport layer, an emission layer, an electron transport layer, and a cathode stacked in that order. A fifth layer arrangement includes an anode, a hole transport layer, an emission layer, a hole/exciton blocking layer, an electron transport layer, and a cathode stacked in that order.

The iridium complex of this embodiment may be used in one of the layers in the first to fifth layer arrangements described above.

The organic compound contained in the hole injection layer or the hole transport layer may be a compound having a high hole mobility. The organic compound may be a low-molecular compound or a high-molecular compound. Examples of the organic compound include triarylamine derivatives, phenylenediamine derivatives, stilbene derivatives, phthalocyanine derivatives, porphyrin derivatives, poly(vinyl carbazole), poly(thiophene), and other conductive polymers. Examples thereof are as follows.

[Chem. 16]

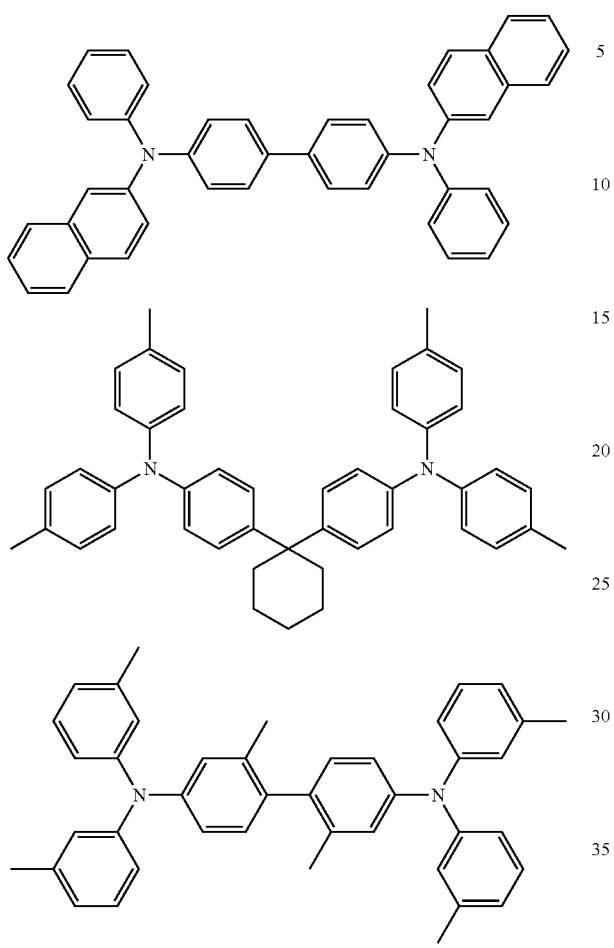

The organic compound included in the electron injection layer or the electron transport layer is selected by considering the balance between the hole mobility of the compound included in the hole injection layer or the hole transport layer and that of the organic compound included in the electron injection layer or the electron transport layer. Examples thereof include oxadiazole derivatives, oxazole derivatives, pyrazine derivatives, triazole derivatives, triazine derivatives, quinoline derivatives, quinoxaline derivatives, phenanthroline derivatives, and organic aluminum complexes. Examples thereof are as follows:

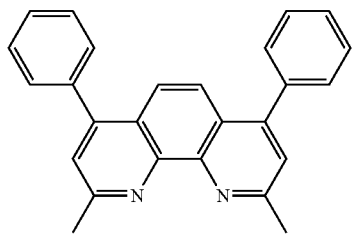

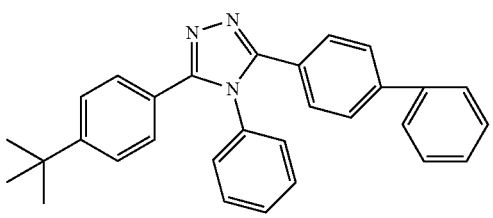

The emission layer may include one organic compound or two or more organic compounds. When the emission layer includes two or more organic compounds, they may be a host material and a guest material. A host material is a main component of the emission layer and its weight ratio is larger than that of the guest material. The amount of the guest material, which is the auxiliary component, relative to the total weight of the emission layer is 0.01 wt. % or more and 20 wt. % or less and preferably 0.5 wt. % or more and 10 wt. % or less. The guest material may be an emission material that determines the color of emission. When the emission layer includes two or more organic compounds, they may be a host material, a guest material, an emission assisting material, and a charge injection material.

The host material may be a material in which carriers of both holes and electrons move smoothly. Alternatively, the host material may be a material that has a lowest triplet excitation energy level T1 higher than that of the emission material in order to efficiently use the excitons generated in the emission layer for emission. Examples of the host material include fused compounds (e.g., fluorene derivatives, naphthalene derivatives, carbazole derivatives, quinoxaline derivatives, and quinoline derivatives), organic aluminum complexes such as tris(8-quinolinolato)aluminum, organic zinc complexes, and polymer derivatives such as triphenylamine derivatives, poly(fluorene) derivatives, and poly(phenylene) derivatives. Examples thereof are as follows:

[Chem. 17]

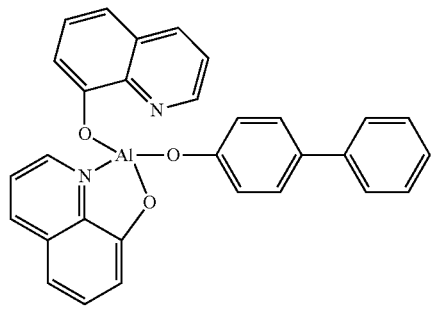

[Chem. 18]

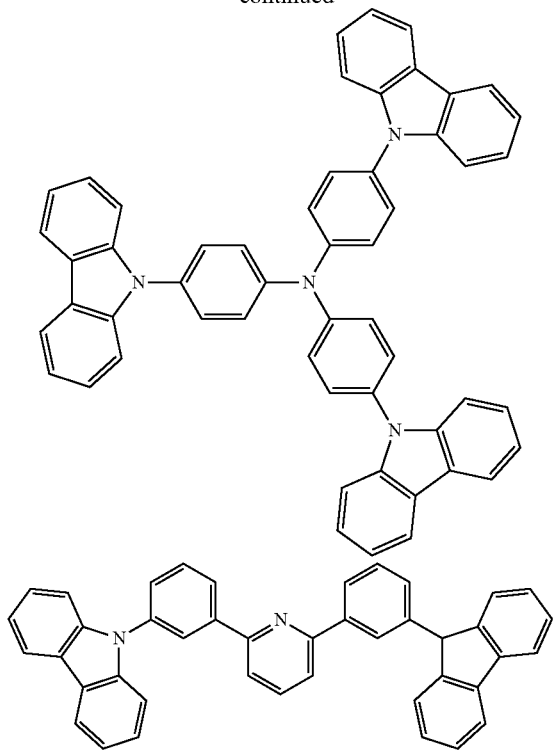

A material having a work function as large as possible may be used in the anode. Examples of such a material include single metals such as gold, platinum, silver, copper, nickel, palladium, cobalt, selenium, vanadium, and tungsten or alloys thereof, and metal oxides such as tin oxide, zinc oxide, indium oxide, indium tin oxide (ITO), and indium zinc oxide. Conductive polymers such as polyaniline, polypyrrole, and polythiophene may also be used. These electrode substances may be used alone or in combination. The anode may be constituted by one layer or two or more layers.

The cathode may be composed of a material having a small work function. Examples of such a material include alkali metals such as lithium, alkaline earth metals such as calcium, and single metals such as aluminum, titanium, manganese, silver, lead, and chromium. The single metals may be combined and used as alloys. For example, magnesium-silver, aluminum-lithium, and aluminum-magnesium alloys and the like can be used. Metal oxides such as indium tin oxide (ITO) can also be used. These electrode substances may be used alone or in combination. The cathode may be constituted by one layer or two or more layers.

Examples of the method for forming a layer containing the iridium complex and other layers containing organic compounds include thin-film forming methods such as vacuum vapor deposition, ionization deposition, sputtering, plasma coating, and coating using an adequate solvent (spin-coating, dipping, casting, a Langmuir Blodgett method, and an ink jet method). When layers are formed by vacuum vapor deposition of solution coating, crystallization is suppressed and the stability over time can be improved. When layers are formed by coating, layers may be formed by using an adequate binder resin in combination.

Examples of the binder resin include polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or in combination of two or more as a copolymer. If needed, known additives such as a plasticizer, an antioxidant, and an ultraviolet absorber may be used in combination.

The organic light-emitting device of this embodiment can be used in display apparatuses and lighting apparatuses. The organic light-emitting device can also be used as exposure light sources of image-forming apparatuses and backlights of liquid crystal display apparatuses.

A display apparatus includes a display unit that includes the organic light-emitting device of this embodiment. The display apparatus can display images by using the organic light-emitting device.

The display unit may include pixels and each pixel may include the organic light-emitting device of this embodiment. The display apparatus can be used as an image display apparatus of a personal computer, etc.

The display apparatus may be used in a display unit of an imaging apparatus such as digital cameras and digital video cameras. An imaging apparatus includes the display unit and an imaging unit having an imaging optical system for capturing images.

A display apparatus may include an image input unit and a display unit. The image input unit may be an imaging optical system mentioned above, a light-detecting unit such as a charge coupled device (CCD), a unit that receives a memory card or the like, a scanner, or the like. Examples of the apparatuses that have the organic light-emitting device of the embodiment in the display unit include digital cameras and digital video cameras described above, and multifunctional image-forming apparatuses that have a scanner function and an image output function. A multifunctional image-forming apparatus may be an image-forming apparatus of an ink jet type or an electrophotographic type.

Next, a display apparatus that uses an organic light-emitting device according to an embodiment of the present invention is described.

Figure 3:
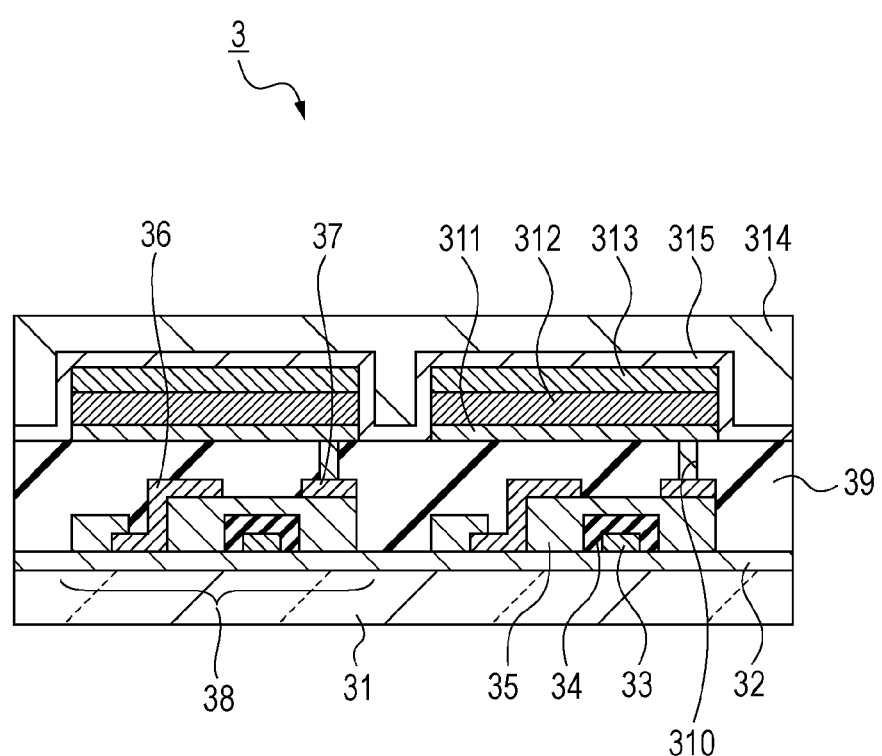
FIG. 3 is a schematic cross-sectional view of an organic light-emitting device and a TFT element which is a switching element coupled to the organic light-emitting device.

FIG. 3 is a schematic cross-sectional view of a display apparatus showing an organic light-emitting device functioning as a pixel and a switching element coupled to the organic light-emitting device. In the drawing, the switching element is a thin film transistor (TFT) element. Alternatively, the switching element may be a metal-insulator-metal (MIM) element.

A display apparatus 3 includes a substrate 31 composed of, for example, glass and a moisture-proof film 32 for protecting the TFT element or the organic compound layer on the substrate 31. The display apparatus 3 also includes a metal gate electrode 33 composed of chromium or the like and a gate insulating film 34.

A TFT element 38 includes a semiconductor film 35, a drain electrode 36, and a source electrode 37. An insulating film 39 is formed over the TFT element 38. The source electrode 37 is connected to an anode 311 of an organic light-emitting device through a contact hole (through hole) 310.

An organic compound layer 312 is illustrated in the drawing as a single layer for the purposes of simplification but is a multilayer organic compound layer. A first protective layer 314 and a second protective layer 315 are provided on a cathode 313 to suppress deterioration of the organic light-emitting device.

The luminance of the light emitted from the organic light-emitting device is controlled by the TFT element. When plural organic light-emitting devices are provided in the surface, an image can be displayed by controlling the luminance of the emission.

EXAMPLES

Examples will now be described.

Example 1

Synthesis of Example Compound 1-1

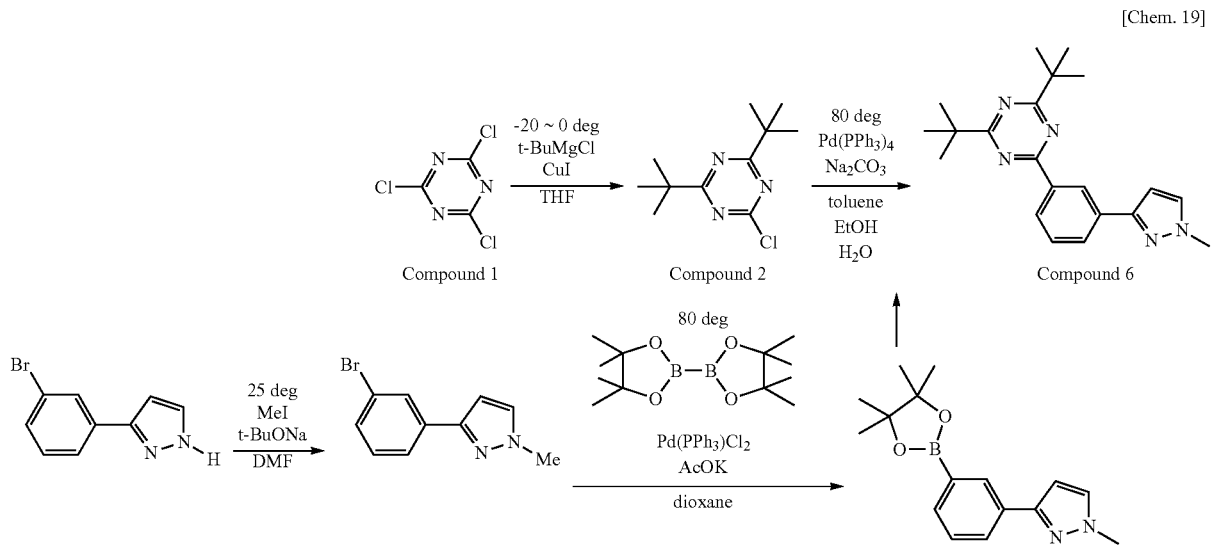

Synthesis of Intermediate Compound 2

Into a 500 ml three-neck flask, 20.0 g (108 mmol) compound 1, 1.03 g (5.42 mmol) copper iodide, and 100 ml THF were placed and cooled to −20° C. Nitrogen bubbling was performed for 10 minutes and 160 ml (320 mmol) of a 2 mol/L tert-butyl magnesium chloride THF solution was added dropwise at a rate at which the temperature of the reaction solution did not exceed 0° C. Upon completion of dropwise addition, the mixture was stirred for 24 hours at room temperature. Elimination of the raw materials and generation of a new compound were confirmed by gas chromatography. Separation was conducted three times with tert-butyl methyl ether/saturated ammonium chloride solution, followed by separation with tert-butyl methyl ether/water, and the organic phase was recovered. The organic phase was dried over magnesium sulfate, concentrated, and purified by silica gel column chromatography (developing solvent: heptane:toluene=6:1). The target substance was concentrated to obtain 19.5 g (85.6 mmol) of compound 2 (yield: 80.0%). When analyzed with a gas chromatograph-mass spectrometer (GS-MS), a peak was observed at m/z=227. The product was confirmed to be the target substance.

Synthesis of Intermediate Compound 4

Into 300 ml round-bottomed flask, 7.00 g (31.4 mmol) compound 3, 3.30 g (34.5 mmol) sodium tert-butoxide, and 100 ml DMF were placed. Thereto, 2.15 ml (34.5 mmol) of iodomethane was added dropwise and the mixture was stirred for 24 hours at room temperature. Elimination of the raw materials and generation of a new compound were confirmed by thin layer chromatography (TLC). The reaction solution was concentrated and separated three times with toluene/water to recover the organic phase. The organic phase was dried over magnesium sulfate, concentrated, and purified by silica gel column chromatography (developing solvent: toluene:heptane:ethyl acetate=10:10:1). The target substance was concentrated to obtain 5.21 g (22.0 mmol) of compound 4 (yield: 70.0%). Nine protons were assigned by $^1$H-NMR (CDCl$_3$: 7.95 (s, 1H), 7.71 ppm (d, 1H), 7.42-7.39 ppm (m, 2H), 7.26 ppm (t, 1H), 6.53 ppm (d, 1H), 3.96 ppm (s, 3H)).

When analyzed with a gas chromatograph-mass spectrometer (GS-MS), a peak was observed at m/z=236. The product was confirmed to be the target substance.

Synthesis of Intermediate Compound 5

Into a 500 ml round-bottomed flask, 5.00 g (21.1 mmol) compound 4, 5.89 g (23.2 mmol) bis(pinacolato)diboron, and 300 ml dioxane were placed and nitrogen bubbling was conducted for 15 minutes. To the resulting mixture, 296 mg (0.422 mmol) bis(triphenylphosphine)palladium(II) dichloride and 6.20 g (63.0 mmol) potassium acetate were added and the mixture was stirred under heating at 80° C. for 8 hours. Elimination of the raw materials and generation of a new compound were confirmed by thin layer chromatography (TLC). Separation was conducted twice with toluene/water to recover the organic phase. The organic phase was dried over magnesium sulfate, concentrated, and purified by silica gel column chromatography (developing solvent: toluene:heptane:ethyl acetate=1:4:1). The target substance was concentrated to obtain 4.20 g (14.8 mmol) of compound 5 (yield: 75.0%). Twenty seven protons were assigned by $^1$H-NMR to confirm generation of the target substance (CDCl$_3$: 8.19 (s, 1H), 7.94 ppm (d, 1H), 7.74 ppm (d, 1H), 7.40 ppm (t, 1H), 7.37 ppm (d, 1H), 6.60 ppm (d, 1H), 3.95 ppm (s, 3H), 1.38-1.32 ppm (m, 18H)).

Synthesis of Intermediate Compound 6

Into a 500 ml round-bottomed flask, 2.65 g (11.6 mmol) compound 2, 3.00 g (10.6 mmol) compound 5, 150 ml toluene, 75 ml ethanol, and 150 ml water were placed and nitrogen bubbling was conducted for 15 minutes. To the resulting mixture, 366 mg (0.317 mmol) tetrakis(triphenylphosphine)palladium(0) and 31 g (292 mmol) sodium carbonate were added and the mixture was stirred under heating at 80° C. for 8 hours. Elimination of the raw materials and generation of a new compound were confirmed by thin layer chromatography (TLC). Separation was conducted twice with toluene/water to recover the organic phase. The organic phase was dried over magnesium sulfate, concentrated, and purified by silica gel column chromatography (developing solvent: toluene:heptane:ethyl acetate=1:3:1). The target substance was concentrated to obtain 3.56 g (9.75 mmol) of compound 6 (yield: 92.0%). Twenty seven protons were assigned by $^1$H-NMR (CDCl$_3$: 8.96 (s, 1H), 8.56 ppm (d, 1H), 8.05 ppm (d, 1H), 7.55 ppm (t, 1H), 7.46 ppm (d, 1H), 6.69 ppm (d, 1H), 3.96 ppm (s, 3H), 3.96 ppm (s, 3H), 1.40-1.35 ppm (m, 18H)).

[Chem. 20]

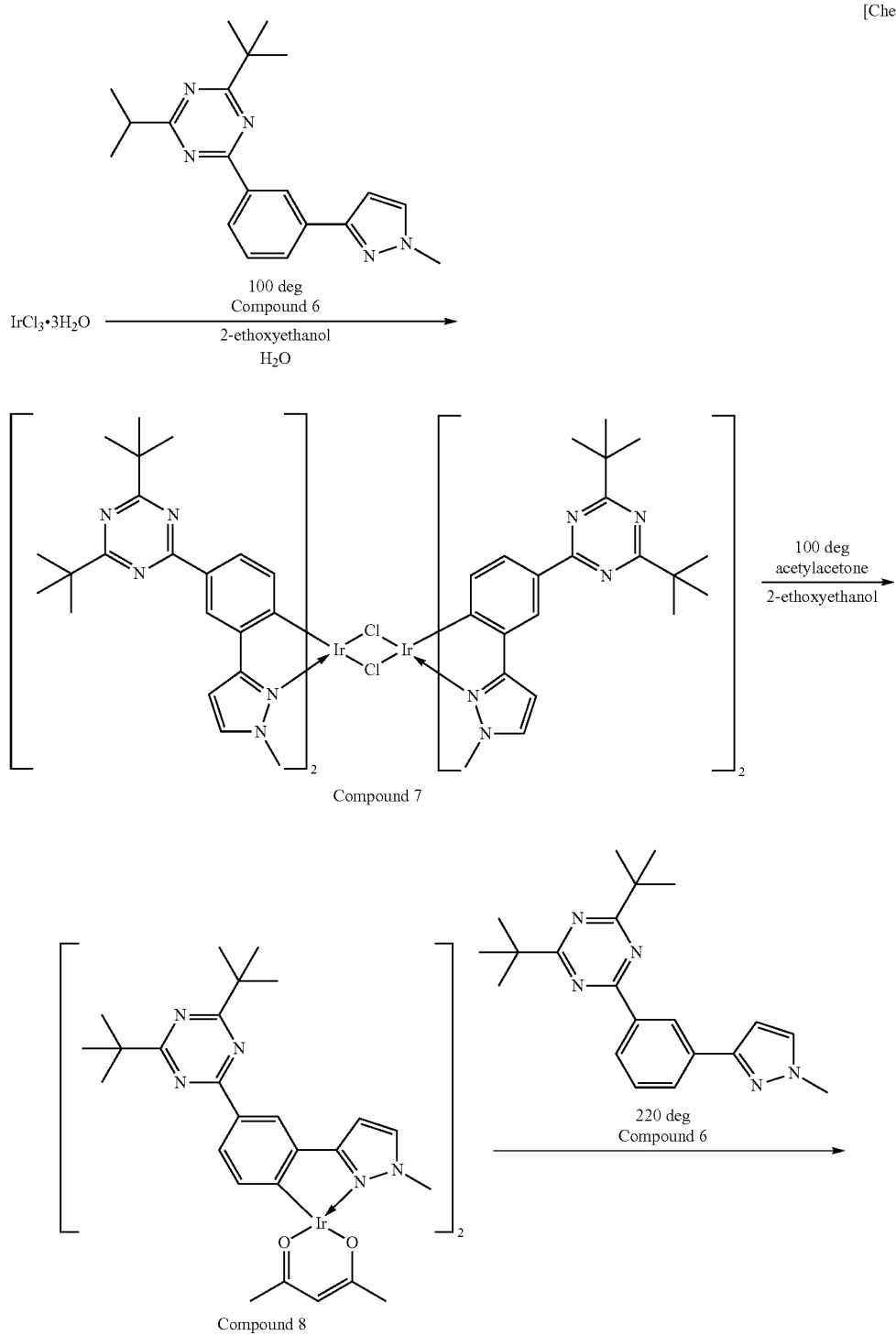

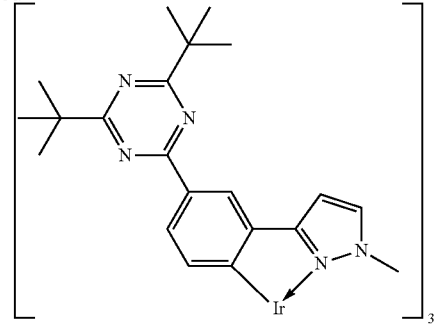

Example compound 1-1

Synthesis of Intermediate Compound 7

To a 100 ml round-bottomed flask, 1.00 g (2.74 mmol) compound 6, 439 mg (1.24 mmol) iridium trichloride trihydrate, 20 ml 2-ethoxyethanol, and 7 ml water were placed. After conducting nitrogen bubbling for 10 minutes, the mixture was stirred under heating at 100° C. for 12 hours. A small amount of sample was taken from the reaction solution and analyzed by $^1$H-NMR to confirm generation of a new compound. After the reaction solution was returned to room temperature, the precipitates were filtered out. The filtrate was washed with 20 ml methanol and filtered to obtain 774 mg (0.422 mmol) of compound 7 (yield: 68.0%). One hundred and four protons were assigned by $^1$H-NMR to confirm generation of the target substance (CDCl$_3$: 8.45 (s, 4H), 7.76 ppm (d, 4H), 7.61 ppm (d, 4H), 6.86 ppm (d, 4H), 6.05 ppm (d, 4H), 3.84 ppm (s, 12H), 1.38-1.32 ppm (m, 72H)).

Synthesis of Intermediate Compound 8

To a 100 ml round-bottomed flask, 500 mg (0.272 mmol) compound 7, 272 µl (2.72 mmol) acetyl acetone, 144 mg (2.72 mmol) sodium carbonate, and 15 ml 2-ethoxyethanol were placed. The mixture was stirred under heating at 100° C. for 12 hours. A small amount of sample was taken from the reaction solution and analyzed by $^1$H-NMR to confirm generation of a new compound. After the reaction solution was returned to room temperature, 30 ml water was added thereto, the mixture was stirred for 10 minutes, and precipitates were filtered out. The filtrate was washed with 20 ml methanol and filtered to obtain 446 mg (0.452 mmol) of compound 8 (yield: 83.0%). Fifty three protons were assigned by $^1$H-NMR to confirm generation of the target substance (CDCl$_3$: 8.50 (s, 2H), 7.85 ppm (d, 2H), 7.54 ppm (d, 2H), 6.76 ppm (d, 2H), 6.28 ppm (d, 2H), 5.36 ppm (s, 1H), 3.84 ppm (s, 6H), 1.38-1.32 ppm (m, 36H)).

Synthesis of Example Compound 1-1

Into a 10 ml round-bottomed flask, 100 mg (0.101 mmol) compound 8 and 1.00 g (2.74 mmol) compound 6 were placed. The mixture was stirred under heating at 220° C. for 24 hours. Elimination of the raw materials and generation of a new compound were confirmed by thin layer chromatography (TLC). The reaction solution was washed with 30 ml toluene and filtered. This was repeated three times to obtain 37.5 mg (0.0303 mmol) Example compound 1-1 (yield: 30.0%). Seventy eight protons were assigned by $^1$H-NMR (DMSO-d$_6$: 8.47 (s, 3H), 7.87 ppm (d, 3H), 7.73 ppm (d, 3H), 6.85 ppm (d, 3H), 6.65 ppm (d, 3H), 3.28 ppm (s, 9H), 1.41-1.35 ppm (m, 54H)). A peak was observed at m/z=1238 by matrix-assisted laser desorption ionization-time-of-flight mass spectroscopy (MALDI-TOF-MS), which confirmed generation of a facial isomer of the target compound.

The emission spectrum of Example compound 1-1 at room temperature was measured. Measurement was conducted using 1×10$^{-5}$ mol/l toluene solution and F-4500 produced by Hitachi Corporation at an excitation wavelength of 350 nm. Example compound 1-1 had a spectrum that has a maximal wavelength at 468 nm at room temperature. The half width of the emission spectrum was 47 nm and the chroma according to Commission Internationale d'Eclairage (CIE) standard colorimetric system was x=0.13, y=0.25.

Figure 2:
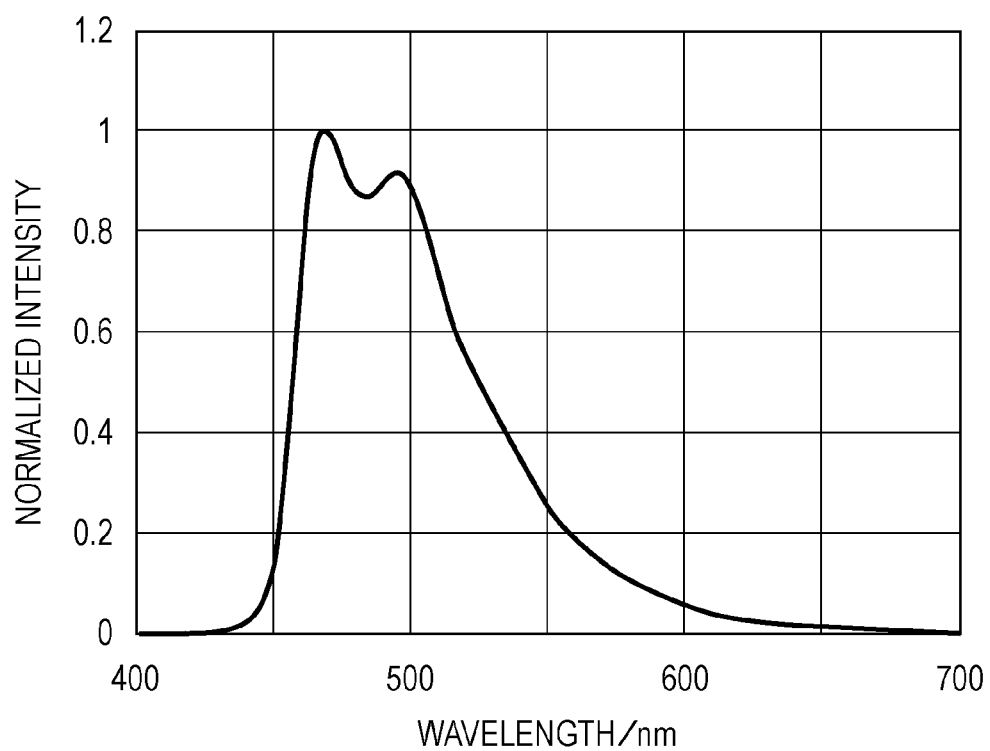
FIG. 2 is an emission spectrum diagram of Compound 9 according to a comparative example.

For comparison, a spectrum of compound 9, which is a common blue light-emitting material and an iridium complex represented by the structural formula below, is shown in FIG. 2.

[Chem. 21]

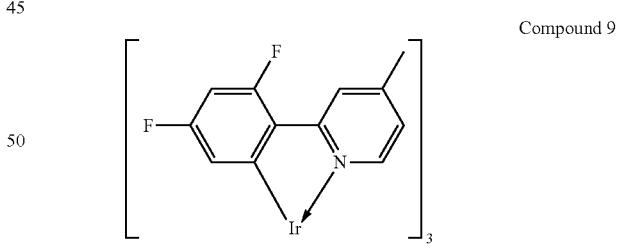

Compound 9

This compound also has an emission maxima at 468 nm. The half width of the emission spectrum was 66 nm and the chroma according to CIE standard colorimetric system was x=0.16, y=0.34.

The measurements show that Example compound 1-1 has a half width 19 nm smaller than that of compound 9.

Example compound 1-1 is excellent as a display-use blue light-emitting material since its emission color is close to blue in a National Television System Committee (NTSC) colorimetry system (x=0.14, y=0.08 in CIE system) than that of compound 9. In other words, Example compound 1-1 has an emission spectrum with a small half width and is thus favorable as a blue light-emitting material.

Example 2

Preparation of Organic Light-Emitting Device Using Example Compound 1-1

A glass substrate with an anode formed by sputter-depositing indium tin oxide (ITO) to a thickness of 120 nm was used as a transparent conductive support substrate. The substrate was ultrasonically washed with acetone and then with isopropyl alcohol (IPA), washed with boiling IPA, and then dried. The substrate was then subjected to UV/ozone washing and used as the transparent conductive support substrate.

A hole injection layer 30 nm in thickness was formed on the transparent conductive support substrate by spin-coating with a chloroform solution of compound 10.

The organic layers and electrode layers described below were continuously vacuum vapor-deposited in a vacuum chamber at $10^{-5}$ Pa by resistive heating to prepare a device.

Hole transport layer (20 nm): compound 10

Emission layer (40 nm): Example compound 1-1 (weight density: 10%) and compound 11 (weight density 90%)

Electron transport layer (30 nm): compound 12

Metal electrode layer 1 (0.5 nm): LiF

Metal electrode layer 2 (150 nm): Al

The structural formulae of compounds 10, 11, and 12 are as follows.

[Chem. 22]

Compound 10

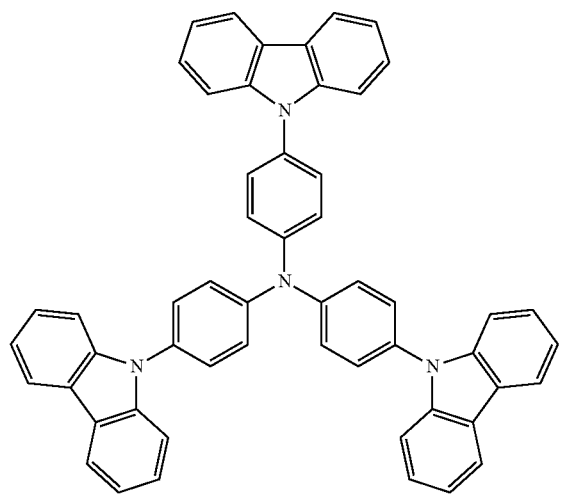

Compound 11

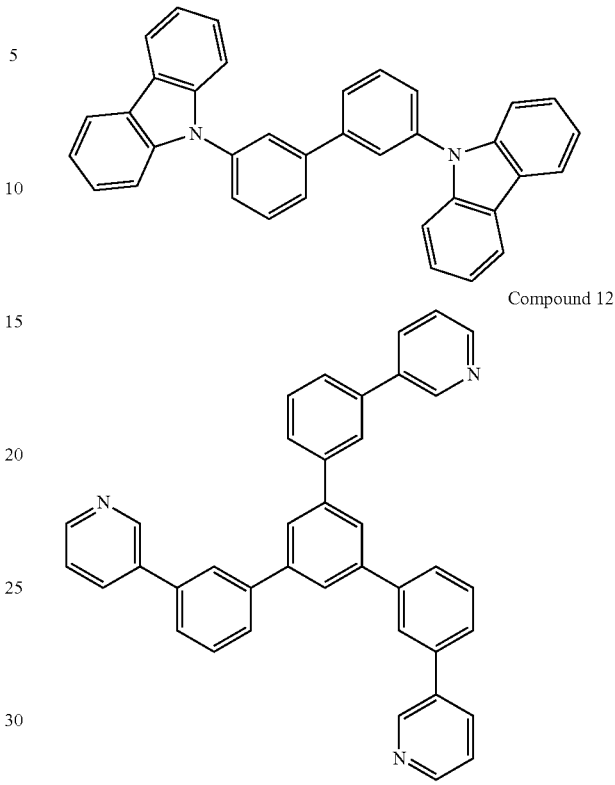

Compound 12

The properties of the obtained organic light-emitting device were measured. In particular, the current-voltage characteristic of the device was measured with a pA meter 4140B produced by Hewlett-Packard Company, and the luminance of the emission from the organic light-emitting device was measured with BM7 produced by Topcon Corporation. The organic light-emitting device exhibited a blue emission of x=0.19, y=0.36 according to the CIE color system at a luminance of 1000 cd/m². A high emission efficiency of 21.4 cd/A and an external quantum yield of 9.6% were achieved. When a voltage was applied to the device in a nitrogen atmosphere for 100 hours, continuation of satisfactory emission was confirmed.

As discussed above, the iridium complexes according to embodiments of the present invention are novel compounds that offer high quantum yields and exhibit emission suitable for blue. Organic light-emitting devices having good emission characteristics can be formed by using these iridium complexes.

The present invention provides an iridium complex that has good blue emission characteristics. An organic light-emitting device having good emission characteristics is also provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-278967, filed Dec. 8, 2009, which is hereby incorporated by reference herein in its entirety.

The invention claimed is:

1. An iridium complex represented by general formula (1):

[Chem. 1]

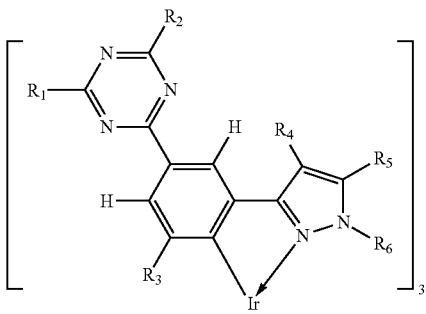

(1)

where $R_1$ and $R_2$ each independently represent a group selected from a tert-butyl group, an adamantyl group, and a bicyclooctyl group; $R_3$ represents one selected from a hydrogen atom, a halogen atom, and a cyano group; $R_4$ and $R_5$ each independently represent one selected from a hydrogen atom, a halogen atom, a cyano group, an alkyl group, an alkoxy group, and an amino group; and $R_6$ represents an alkyl group.

2. The iridium complex according to claim 1, wherein $R_1$ and $R_2$ each represent a tert-butyl group.

3. The iridium complex according to claim 1, wherein $R_6$ represents a methyl group.

4. The iridium complex according to claim 1, wherein the iridium complex emits blue light.

5. A material for an organic light-emitting device, comprising the iridium complex according to claim 1.

6. An organic light-emitting device comprising:
a pair of electrodes; and
an organic compound layer interposed between the pair of electrodes, the organic compound layer containing the iridium complex according to claim 1.

7. The organic light-emitting device according to claim 6, wherein the organic compound layer is an emission layer, the emission layer contains a host material and a guest material, and the guest material is the iridium complex.

8. A display apparatus comprising:
a plurality of pixels each including the organic light-emitting device according to claim 6 and a switching element coupled to the organic light-emitting device.